US00PP12879P2

(12) United States Plant Patent
Roberson

(10) Patent No.: US PP12,879 P2
(45) Date of Patent: Aug. 27, 2002

(54) LANTANA PLANT NAMED 'ROBMORNPIN'

(76) Inventor: Robert J. Roberson, 31706 E. Pink Hill Rd., Grain Valley, MO (US) 64029

( * ) Notice: Subject to any disclaimer, the term of this patent is extended or adjusted under 35 U.S.C. 154(b) by 39 days.

(21) Appl. No.: 09/837,569

(22) Filed: Apr. 18, 2001

(51) Int. Cl.[7] ..... A01H 5/00
(52) U.S. Cl. ..... Plt./227
(58) Field of Search ..... Plt./227

(56) References Cited

U.S. PATENT DOCUMENTS

PP9,837 P * 3/1997 Roberson ..... Plt./227
PP10,156 P * 12/1997 Roberson ..... Plt./227

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Lantana plant named 'Robmornpin', characterized by its outwardly spreading plant habit; rapid growth rate; dark green foliage; freely flowering habit; and yellow, dark pink and red-colored flowers.

1 Drawing Sheet

BACKGROUND OF THE INVENTION

The present Invention relates to a new and distinct cultivar of Lantana plant, botanically known as *Lantana camara*, and hereinafter referred to by the cultivar name 'Robmornpin'.

The new Lantana is a product of a planned breeding program conducted by the Inventor in Grain Valley, Mo. The objective of the breeding program is to create freely-flowering Lantanas that do not produce seed. The new Lantana originated from a cross made by the Inventor in 1995 of the Lantana cultivar 'Patriot Hot Country', not patented, as the female, or seed parent, with an unidentified proprietary Lantana selection as the male, or pollen parent. The new Lantana was selected as a single plant from the resulting progeny by the Inventor in a controlled environment in Grain Valley, Mo., on the basis of its yellow, dark pink and red-colored flowers.

Asexual reproduction of the new cultivar by terminal cuttings taken in Lompoc, Calif. since September, 1999, has shown that the unique features of this new Lantana are stable and reproduced true to type in successive generations.

SUMMARY OF THE INVENTION

Plants of the cultivar 'Robmornpin' have not been observed under all possible environmental conditions. The phenotype may vary somewhat with variations in environment and culture such as temperature, light intensity, daylength, water status, and/or fertilizer rate or type without, however, any variance in genotype.

The following traits have been repeatedly observed and are determined to be the unique characteristics of 'Robmornpin'. These characteristics in combination distinguish 'Robmornpin' as a new and distinct cultivar:

1. Outwardly spreading plant habit.
2. Rapid growth rate.
3. Dark green foliage.
4. Freely flowering habit.

5. Yellow, dark pink and red-colored flowers.

Plants of the new Lantana differ from plants of the parents and other known cultivars of Lantana primarily in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Lantana.

The photograph at the top of the sheet comprises a side perspective view of a typical plant of 'Robmornpin'.

The photograph at the bottom of the sheet comprises a close-up view of typical inflorescences and leaves of 'Robmornpin'.

DETAILED BOTANICAL DESCRIPTION

In the following description, color references are made to The Royal Horticultural Society Colour Chart except where general terms of ordinary dictionary significance are used. Plants grown for 16-weeks in 15-cm containers and pinched once were used for the photographs and following description. Plants were grown in a polycarbonate-covered greenhouse in Lompoc, Calif. during the spring with day temperatures ranging from 18 to 24° C., night temperatures ranging from 16 to 18° C., and light levels ranging from 4,000 to 8,000 foot-candles.

Botanical classification: *Lantana camara* cultivar 'Robmornpin'.

Parentage:

*Female parent.*—*Lantana camara* cultivar 'Patriot Hot Country', not patented.

*Male parent.*—Unidentified proprietary *Lantana camara* selection, not patented.

Propagation:

*Type cutting*.—Terminal cuttings.

*Time to initiate roots, summer*.—About 7 to 10 days at 27° C.

*Time to initiate roots, winter*.—About 10 to 14 days at 23° C.

*Time to develop roots, summer*.—About 28 to 35 days at 27° C.

*Time to develop roots, winter*.—About 35 to 42 days at 23° C.

*Root description*.—Fibrous.

*Rooting habit*.—Freely branching.

Plant description:

*Form*.—Flowering subshrub; initially upright, then outwardly spreading. Freely branching; two lateral branches potentially forming at every node; pinching enhances lateral branch development.

*Plant height*.—About 32 cm.

*Plant diameter*.—About 65 cm.

*Vigor*.—Vigorous, rapid growth rate.

*Lateral branches*.—Length: About 35.5 cm. Diameter: About 5 mm. Internode length: About 7 cm. Aspect: Initially upright, then bending about 90° from upright. Strength: Flexible, but strong. Texture: Rough, coarse. Color: Young: 144A. Woody: 165B.

*Foliage description*.—Leaves simple, generally symmetrical and long-persisting; opposite. Length, largest leaves: About 10 cm. Width, largest leaves: About 7.8 cm. Shape: Ovate to oval. Apex: Acute. Base: Acute to obtuse. Margin: Crenate to serrate. Texture, both surfaces: Leathery, rough, coarse; slightly rugose. Lower surface, pubescent. Venation pattern: Pinnate, laterals arcuate. Fragrance: Pungent, mint-like; pleasant. Color: Young foliage, upper surface: 146A. Young foliage, lower surface: 146B. Mature foliage, upper surface: 147A; venation, 146B. Mature foliage, lower surface: 147B; venation, 147C. Petiole length: About 2 cm. Petiole diameter: About 2.5 mm. Petiole color: 146B.

Flower description:

*Flower type and habit*.—Small salverform flowers arranged in axillary umbels; flowers face mostly upward or outward. Flowers self-cleaning. Very freely flowering with potentially two inflorescences per node; typically about 30 to 32 flowers per umbel.

*Natural flowering season*.—Spring until frost in the autumn; flowering continuous and consistent.

*Flower longevity on the plant*.—About 5 to 7 days.

*Fragrance*.—Faint, spicy, pleasant.

*Inflorescence diameter*.—About 4.2 cm.

*Inflorescence height*.—About 2.5 cm.

*Flowers*.—Appearance: Flared trumpet, corolla fused, four-parted; flowers roughly rectangular in shape. Diameter: About 1.2 cm by 1 cm. Corolla tube length: About 1.7 cm.

*Flower buds* (*showing color*).—Length: About 8 mm. Diameter: Apex: About 2.5 mm. Base: About 1 mm. Shape: Elongate, oblong. Color: 37B to 37C.

*Corolla*.—Arrangement/appearance: Single whorl of four petals, fused into flared trumpet. Petal length from throat: About 6 mm. Petal width: Upper and lower petals, about 7 mm; lateral petals, about 5 mm. Petal shape: Irregularly ovoid to almost orbicular. Petal apex: Rounded with slight emargination. Petal margin: Entire. Petal texture: Smooth, velvety. Color: Petal, upper surface, when opening: 10B; throat, 14A. Petal, lower surface, when opening: 10D; tube, 50B. Petal, upper surface, fully opened: 63A; with subsequent development, shifting to 67B, then to 45C; throat, 28B. Petal, lower surface and tube, fully opened: 63C; tube, 50B.

*Calyx*.—Arrangement/appearance: One single calyx tube per flower. Calyx length: About 2 mm. Calyx width: About 1 mm. Apex: Broadly acute. Texture: Pubescent. Color, both surfaces: 144D.

*Peduncles*.—Length: About 8.25 cm. Diameter: About 2 mm. Angle: About 45° from the stem. Strength: Flexible, but strong. Color: 144A.

*Pedicels*.—Length: Less than 0.5 mm. Diameter: Less than 0.25 mm. Color: Close to 144A.

*Reproductive organs*.—Stamens: Quantity/arrangement: Four per flower, adnate to floral tube. Anther shape: Ovoid. Anther length: Less than 1 mm. Anther color: 22B. Pollen amount: Scarce. Pollen color: 22B. Pistils: Quantity: One per flower. Pistil length: About 5 mm. Stigma shape: Bilobed. Stigma color: 148C. Style color: About 3.5 mm. Style color: 148D. Ovary color: 144C.

*Seed*.—Seed production has not been observed.

Disease/pest resistance: Plants of the new Lantana have not been noted to be resistant to pathogens or pests common to Lantana.

Weather tolerance: Plants of the new Lantana have been observed to be tolerant to rain and wind.

It is claimed:

1. A new and distinct cultivar of Lantana plant named 'Robmornpin', as illustrated and described.

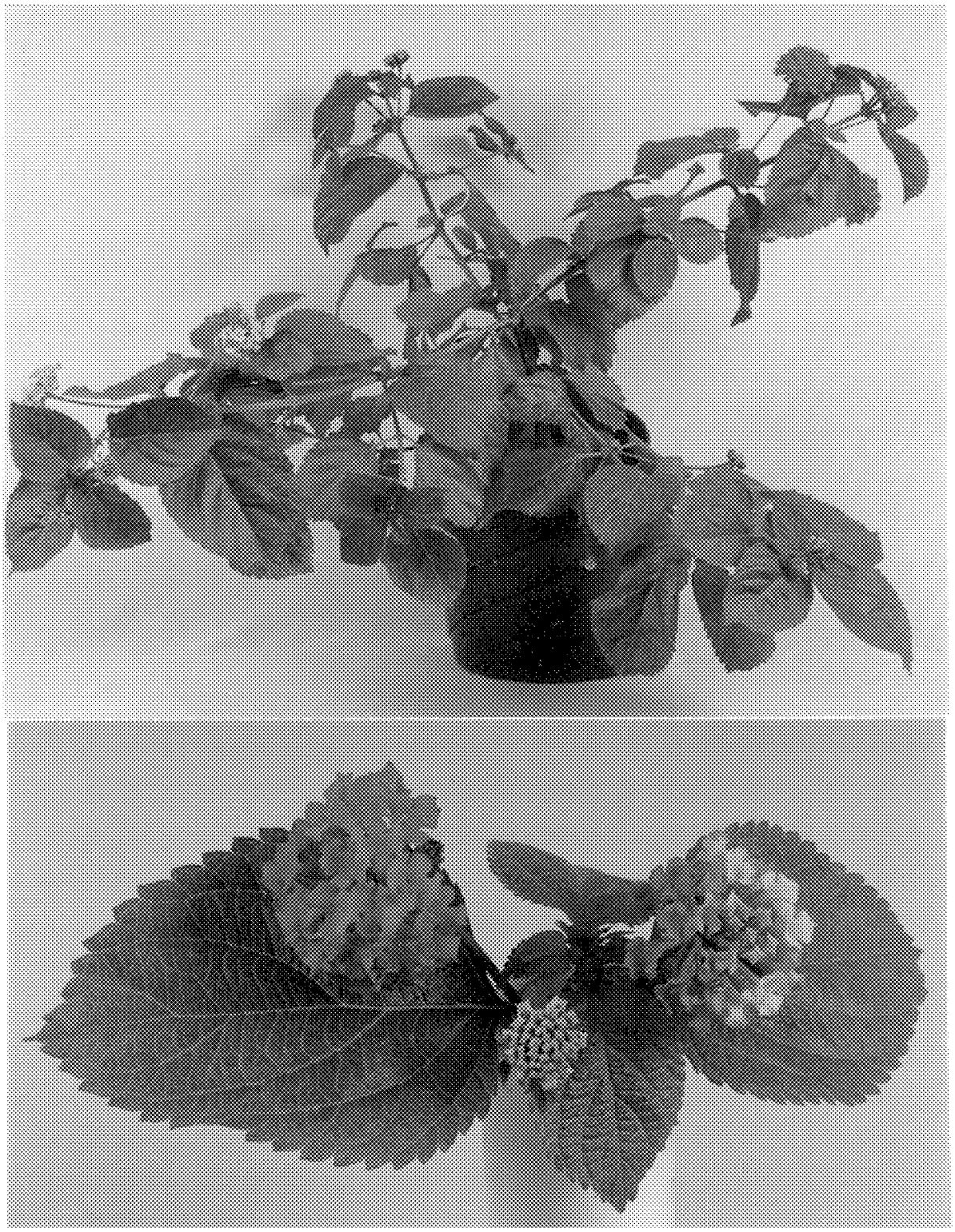

* * * * *